United States Patent [19]

Schlom

[11] Patent Number: 5,183,756
[45] Date of Patent: Feb. 2, 1993

US005183756A

[54] MONOCLONAL ANTIBODY (D612) HAVING SELECTIVE REACTIVITY FOR GASTROINTESTINAL CARICINOMAS AND METHOD FOR EMPLOYING THE SAME

[75] Inventor: Jeffrey Schlom, Potomac, Md.

[73] Assignee: The United States of America as represented by the Department of Health and Human Services, Washington, D.C.

[21] Appl. No.: 715,748

[22] Filed: Jun. 18, 1991

Related U.S. Application Data

[63] Continuation of Ser. No. 234,130, Aug. 19, 1988, abandoned.

[51] Int. Cl.$^5$ .................... C12N 5/20; C07K 15/28; A61K 39/395
[52] U.S. Cl. ........................... 435/240.27; 435/70.21; 435/172.2; 424/85.8; 424/85.91; 530/388.8; 530/388.85
[58] Field of Search ............. 530/388.2, 388.8, 388.85, 530/391.1, 391.7; 424/1.1, 85.8, 85.91, 88, 93; 435/70.21, 172.2, 240.27

[56] References Cited

U.S. PATENT DOCUMENTS 4,579,827 4/1986 Sakamoto ........................... 436/536

OTHER PUBLICATIONS

Herlyn, Proc Natl. Acad. Sci., (Mar. 1979), vol. 76(3):1438-42.

Sears, The Lancet, (1982), pp. 762-765.
Fersten et al., Characterization of the Colorectal Carcinoma-associated Antigen Defined by Monoclonal Antibody D612, Cancer Research. vol. 51, pp. 926-934 (1991).
Gottlinger et al., The Epithelial Cell Surface Antigen 17-1A, A Target for Antibody-Mediated Tumor Therapy: Its Biochemical Nature, Tissue Distribution and Recognition by Different Monoclonal Antibodies, Int. J. Cancer: vol. 38, pp. 47-53 (1986).
Pendurthi, et al.; submitted to Int. J. Cancer; Lymphokine-Activated Killer Cell Cytotoxicity Against Human Colon Carcinomas Enhanced by Monoclonal Antibody D612; Laboratory of Tumor Immunology and Biology, National Cancer Institute, Bethesda, Md.
Pendurthi, et al.; submitted to J. Biol. Res. Mod.; Human Lymphokine-Activated Killer Cells Augment Immunotherapy of Human Colon Carcinoma Xenografts with Monoclonal Antibody D612.
Muraro, et al.; In. J. Cancer: 43, 598-607; A Monomclona Antibody *D612) With Selective Reactivity For Malignant And Normal Gastro-Intestinal Epithelium.

*Primary Examiner*—John J. Doll
*Assistant Examiner*—Robert D. Budens
*Attorney, Agent, or Firm*—Susan S. Rucker

[57] ABSTRACT

The present invention relates to the monoclonal antibody (termed D612) having selective reactivity for gastrointestinal carcinoma and methods for employing the same. A hybridoma producing such antibodies has been prepared.

19 Claims, 3 Drawing Sheets

MONOCLONAL ANTIBODY (D612) HAVING SELECTIVE REACTIVITY FOR GASTROINTESTINAL CARICINOMAS AND METHOD FOR EMPLOYING THE SAME

This is a continuation of application Ser. No. 07/234,130, filed on Aug. 19, 1988, which was abandoned upon the filing hereof.

FIELD OF THE INVENTION

The present invention relates to the generation of a monoclonal antibody (D612) having selective reactivity for gastronintestinal carcinomas, and methods for employing the same.

BACKGROUND OF THE INVENTION

Numerous monoclonal antibodies to antigens associated with gastronintestinal malignancies have been reported. Some of the more widely used monoclonal antibodies include monoclonal antibodies 17-1A (see Herlyn, M. et al, *Proc. Natl. Acad. Sci.* 76:1438-1442 (1979)), 19-9 (see Koprowski, H. et al, *Somat. Cell Genet.* 5:957-972 (1979)), B72.3 (see Colcher, D. et al, *Proc. Natl. Acad. Sci. USA* 78:3199-3202 (1981)), Du-PAN-2 (see Metzgar, R. S. et al, *Cancer Res.* 42:601-608 (1982)), and a variety of monoclonal antibodies directed against carcinoembryonic antigen (see Boyer, C. M. et al, *Antibody, Immunoconjugates and Radiopharmaceuticals*, New York, N.Y., Mary Ann Liebert, Inc., pp. 105-161 (1988) and Muraro, R. et al, *Cancer Res.* 45:5769-5780 (1985)). Moreover, other monoclonal antibodies to colon associated antigens have recently been reported (see Boyer, C. M. et al, *Antibody, Immunoconjugates and Radiopharmaceuticals*, New York, N.Y. Mary Ann Liebert, Inc., pp. 105-161 (1988); Schlom, J. et al, *Important Advances in Oncology*, Philadelphia, Pa., J. B. Lippincott Co., Vol. 1, pp. 170-192 (1984); Nocera, M. et al, *J.N.C.I.* 79:943-948 (1987); Hughes, N. R. et al, *Cancer Res.* 46:2164-2171 (1986); Podolsky, D. K. et al, *J. Clin. Invest.* 77:1263-1271 (1986); and Richman, P. I. et al, *Int. J. Cancer* 39:317-328 (1987)). Of the above monoclonal antibodies, only monoclonal antibody 17-1A is of the IgG$_{2a}$ isotype and also mediates antibody dependent cell mediated cytotoxicity. Monoclonal antibody 17-1A, however, has also shown reactivity to normal adult kidney, thyroid, and pancreas whereas monoclonal antibody D612 does not. Another monoclonal antibody, designated monoclonal antibody CAA, has shown reactivity to both normal and malignant colonic epithelium (see Muraro, R. et al, *Cancer Res.* 39:39-44 (1987)). The molecular weight of the monoclonal antibody CAA-reactive antigen was shown to be >200 kd and its expression correlated with the degree of cellular differentiation of colon carcinomas. The molecular weight of the reactive antigen and the pattern of reactivity to colorectal carcinomas versus normal tissues clearly distinguishes D612 from the monoclonal antibodies described above.

Several large molecular weight antigens associated with normal large intestinal epithelium have been previously described based on detection with polyclonal antibodies. The organ specific CMA (see Gold, D. V., *Cancer Res.* 41:767-772 (1981)) differs from the D612-reactive antigen in two major properties. Unlike D612, expression of CMA in colonic carcinomas is directly related to their differentiation. Moreover, unlike D612, CMA is predominantly located in the normal goblet cell vacuole while in carcinomas, it appears as cytoplasmic droplets; the intestinal M3 antigen (see Bara J. et al, *Br. J. Cancer* 41:201-221 (1980)) is very similar in its localization pattern to that of CMA, suggesting that these antigens may be related to one another. The large intestine mucin antigen (see DeBoer, W. G. R. M. et al, *Path.* 13:547-555 (1981)) differs from the D612-reactive antigen since it is associated with the goblet cell vacuole and D612 is not. Polyclonal antibodies have identified two other colon-associated antigens: the thermolabile CSAp (see Pant, K. D. et al, *Immunol. Comm.* 6:411-421 (1977)) and the thermostabile CSA (see Goldenberg, D. M. et al, *Cancer Res.* 36:3455-3463 (1976)), both of which are not absolutely restricted to the normal colon, since they can also be found at higher levels of the intestinal tract. CSAp is secreted and thus differs from the D612-reactive antigen in this property. (see Pant, K. D. et al, *Cancer* 50:919-926 (1982)). Recently, monoclonal antibodies reactive with normal and neoplastic colonic mucosa have been reported. The cellular localization of the antigen detected by the GNM monoclonal antibody (see Hughes, N. R. et al, *Cancer Res.* 46:2164-2171 (1986)), mainly associated with mucin vacuoles, distinguishes it from the D612-reactive antigen. Two other groups have described several monoclonal antibodies against colonic epithelium based on their distinctive cellular staining patterns. Of 23 antibodies described by Podolsky, D. K. et al, *J. Clin. Invest.* 77:1263-1271 (1986), none showed the same staining characteristics of normal bowel as that of D612. Richman, P. I. et al, *Int. J. Cancer* 39:317-328 (1987) made an extensive evaluation of the normal and neoplastic tissue staining properties of 12 monoclonal antibodies. Of these, the PR.1A3 antibody had a similar but clearly distinct reactivity from that of D612; unlike D612, PR.1A3 exclusively stained the columnar absorptive cell and stained gastric surface eptithelium.

Each of the anti-colon carcinoma monoclonal antibodies described above has potential uses in the study of malignant and normal colon cell populations, and each has potential advantages and limitations in potential clinical applications. Some limitations include: (a) reactivity to a range of normal tissues in addition to colon carcinomas, (b) reactivity to other carcinomas or other malignancies, (c) reactive antigen being shed in the serum of cancer and/or normal patients (for applications other than serum assays), and (d) inadequate reactivity due to heterogeneity of carcinomas cell populations within a given tumor mass, among different masses within the same patient, and among masses from different patients.

The pattern of membrane associated staining, the molecular weight of the reactive antigen in Western blotting, the cell surface antigen expression, and the immunohistochemical studies demonstrating strong reactivity with malignant and normal gastrointestinal tissue and not to any other malignant or normal adult tissue, differentiates monoclonal antibody D612 from other monoclonal antibodies thus far described, and make it more desirable for several clinical applications in the management of human gastrointestinal malignancies.

STATEMENT OF DEPOSIT

The hybridoma cell line which produces the monoclonal antibody D612 has been deposited in the American Type Culture Collection at Rockville, Md., in accord with the requirements of the Budapest Treaty for deposit of patented organisms and biological products and has been assigned ATCC accession number HB 9796. Upon issuance of a patent, the deposited organism will be made available upon request. A viable deposit will be maintained for at least 30 years consistent with provisions of applicable law. All restrictions on public availability of the deposit will be irrevocably removed upon issuance of a patent.

SUMMARY OF THE INVENTION

It is an object of the present invention to provide a monoclonal antibody which has selective binding to a variety of human gastrointestinal carcinomas.

A further object of the present invention is to provide a monoclonal antibody from which highly immunoreactive radiolabeled immunoglobulin (hereinafter "IgG") can be easily obtained for use in in vivo immunodiagnosis and therapy of human gastronintestinal carcinomas.

A still further object of the present invention is to provide a monoclonal antibody from which recombinant antibodies can be obtained for use in in vivo immunodiagnosis and therapy of human gastrointestinal carcinomas.

An additional object of the present invention is to provide a monclonal antibody of the $IgG_{2a}$ isotype which has binding specificity for human gastrointestinal carcinomas for use in conducting monoclonal antibody effector cell mediated cytotoxicity (with or without interleukin-2) (see Rosenberg, S. A. et al, *Science* 223:1412–1415 (1984)) or complement mediated cytotoxicity studies.

Still an additional object of the present invention is to provide methods for diagnosing in vitro and in vivo human gastrointestinal carcinomas and methods for treating human gastrointestinal carcinomas employing this monoclonal antibody.

Other objects and advantages of the present invention will become apparent from the Detailed Description of the Invention.

Unless defined otherwise all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned are incorporated herein by reference.

The term "substantially" as used herein means almost wholly or to a large extent, but not entirely. The term "minimal" means the least possible or substantially inconsequential.

One embodiment provides a method for diagnosing a human gastrointestinal carcinoma or metastases therefrom comprising:

(a) obtaining a body sample, such as body fluid, tissue or biopsy from a patient;

(b) contacting the body sample material with monoclonal antibody D612 of the present invention, immunoreactive fragments or recombinants thereof;

(c) determining the level of binding of monoclonal antibody D612, immunoreactive fragments or recombinants thereof to the body sample material; and (d) comparing the amount of monoclonal antibody D612, immunoreactive fragments or recombinants thereof bound to substances present in the body sample to a control sample or to a predetermined base level, so that a binding greater than the control level is indicative of the presence of primary human gastrointestinal carcinoma or metastases therefrom.

Another embodiment provides a method for diagnosing the presence of a human gastrointestinal carcinoma or metastases therefrom comprising:

(a) administering to a patient monoclonal antibody D612 of the present invention, immunoreactive fragments or recombinants thereof, conjugated to an imaging marker; and (b) exposing the patient to a means for detecting said imaging marker to identify the presence of the imaging marker in order to detect primary human gastrointestinal carcinoma or metastatic sites therefrom in a patient.

A further embodiment provides a method of treating a patient afflicted with a primary human gastrointestinal carcinoma or metastases therefrom, comprising administering to a patient afflicted with primary gastrointestinal carcinoma or metastases arising therefrom, a pharmaceutically effective amount of monoclonal antibody D612 of the present invention, immunoreactive fragments or recombinants thereof either alone, in the presence of interleukin-2 (see Rosenberg, S. A. et al, *Science* 223:1412–1415 (1984)) or conjugated to a therapeutic agent.

DETAILED DESCRIPTION OF THE INVENTION

I. Characteristics of Monoclonal Antibody D612

The monoclonal antibody of the present invention, designated D612, (1) binds to the vast majority of both primary and metastatic colorectal carcinomas and does not bind or binds minimally to other non-gastrointestinal cancers and adult normal tissues other than gastrointestinal epithelium;

(2) binds homogeneously to the cytoplasmic membrane of colorectal carcinoma cells;

(3) binds with high efficiency to well, moderately, and poorly differentiated colorectal carcinoma cells;

(4) binds to a high molecular weight antigen as analyzed by Western blotting;

(5) can mediate antibody dependent cell mediated cytotxicity of human colon carcinoma using human effector cells (a phenomenon that can be potentiated in the presence of interleukin-2) (see Rosenberg, S. A. et al, *Science* 233:1412-1415 (1984)); and (6) can be radiolabeled and can localize human colorectal tumors in vivo.

II. Production of the Monoclonal Antibody

The monoclonal antibody of the present invention is produced by immunizing mice (or other animals such as rats, rabbits, goats, and humans) with a membrane enriched fraction of a moderately differentiated primary colon adenocarcinoma emulsified in an equal volume of complete Freund's adjuvant.

Immunizing the animals, e.g. mice, with the membrane enriched fraction of the colon carcinom, isolating the immunized cells, fusing the immunized cells with mouse myeloma cells (or myeloma cells of other species such as rats, rabbits, goats and humans), all of which are well known in the art and readily available, and culturing the resulting fused cells under conditions which allow for growth of hybridomas, are all conducted by methods described in the prior art (see Herzenberg, L. A. et al., *Handbook of Experimental Immunology*, Oxford, Blackwell pp. 25.1-25.7; Colcher, D. et al, *Proc. Natl. Acad. Sci. (USA)*, 78:3199-3203 (1981); and Muraro, R. et al., *Intl. J. Cancer*, 39:34-44 (1987)).

The resulting hybridomas are then tested to isolate those which produce monoclonal antibodies having selective binding to human colorectal carcinomas and to gastrointestinal epithelium but not to other carcinomas or normal adult human tissues. This screening can be carried out using a solid phase radioimmunoassay (hereinafter "SPRIA") as described in greater detail in the examples provided hereinafter.

The isotype of the monoclonal antibody is determined by means well known in the art (see, for example, Colcher, D. et al, *Cancer Res.* 41:1451-1459 (1981)) and as described in detail in the examples provided herein.

To produce the monoclonal antibody D612, in excess of one thousand three hundred hybridomas were produced by fusing (i) spleen cells of mice immunized with a membrane enriched fraction which was obtained from a human colon carcinoma biopsy, and (ii) the well known and readily available NS-1 mouse myeloma line (ATCC No. TIB 18). From these hybridomas, 27 double cloned hybridomas were selected and characterized by methods described in the examples. The D612 monoclonal antibody that was isolated from one of the resultant cultures displayed a unique reactivity for only colon carcinomas and normal gastrointestinal epithelium.

The recombinant monoclonal antibodies of the present invention can be made by techniques of molecular biology known in the prior art (see Rice, D. et al, *Proc. Natl. Acad. Sci., USA*, 79:7862-7865 (1982); Kurokawa, T. et al, *Nucleic Acids Res.*, 11:3077-3085 (1983); Oi, V. T. et al, *Proc. Natl. Acad. Sci., USA*, 80:825-829 (1983); Boss, M. A. et al, *Nucleic Acids Res.* 12:3791-3806 (1984); Boulianne, G. L. et al, *Nature (London)* 312:643-646 (1984); Cabily, S. et al, *Proc. Natl. Acad. Sci., USA*, 81:3273-3277 (1984); Kenten, J. et al, *Proc. Natl. Acad. Sci., USA*, 81:2955-2959 (1984); Liu, F-T, et al, *Proc. Natl. Acad. Sci., USA*, 81:5369-5373 (1984); Morrison, S. L. et al, *Proc. Natl. Acad. Sci., USA*, 81:6851-6855 (1984); Neuberger, M. S. et al, *Nature (London)*, 312:604-608 (1984); Potter, H. et al, *Proc. Natl. Acad. Sci., USA*, 81:7161-7165 (1984); Neuberger, M. S. et al, *Nature (London)* 314:268-270 (1985); Jones, P. T. et al, *Nature (London)*, 321:522-525 (1986); Oi, V. T. et al, *BioTechniques*, 4:214-221 (1986); Sahagan, B. G. et al, *J. Immunol.*, 137:1066-1074 (1986); Sun, L. K. et al, *Hybridoma* 5 (Suppl. I):S17-S20 (1986); and Sun, L. K. et al, *Proc. Natl. Acad. Sci, USA*, 84:214-218 (1987) all of which are specifically incorporated herein by reference).

The monoclonal antibodies of the present invention can be altered to a chimeric form by substitution, e.g., human constant regions ($F_c$ domains) for mouse constant regions by recombinant DNA techniques known in the art as described in the above cited references. These $F_c$ domains can be of various human isotypes, i.e., $IgG_1$, $IgG_2$, $IgG_4$ or IgM.

In addition, the monoclonal antibodies of the present invention can be altered to affinity modified forms, avidity modified forms, or both, by altering binding sites or altering the hinge region using recombinant DNA techniques known in the art as exemplified in the above cited references.

The recombinant antibody forms can also be fragmented to produce immunoreactive fragments F(ab')$_2$, F(ab') or F(ab) in the same manner as described above in which the monoclonal antibody of the present invention is fragmented.

Accordingly, as used herein, the expression "recombinant antibodies" collectively includes chimeric/-recombinant forms of the monoclonal antibodies of the present invention wherein the $F_c$ domain is substituted for an $F_c$ domain of another species or isotype, affinity modified forms of the monoclonal antibodies of the present invention wherein the binding sites are altered, avidity modified forms of the monoclonal antibodies of the present invention wherein the hinge regions are altered, immunoreactive fragments thereof and combinations thereof.

The monoclonal antibodies of the present invention can be produced in large quantities by injecting a hybridoma producing monoclonal antibodies of the present invention into the peritoneal cavity of pristane-primed mice, and after an appropriate time (about 1-2 weeks), harvesting ascites fluid from the mice. This method yields a very high titer of homogenous monoclonal antibody. Monoclonal antibodies are isolated therefrom by methods well known in the art (see Stramignoni, P. et al, *Intl. J. Cancer* 31:543-552 (1983)). Alternatively, monoclonal antibodies can be produced by culturing a hybridoma capable of producing monoclonal antibodies of the present invention in vitro and isolating secreted monoclonal antibodies from the cell culture medium by methods known in the art (see Colcher, D. et al, *Proc. Natl. Acad. Sci., USA* 78:3199-3203 (1981)). The binding properties of the monoclonal antibodies are discussed in greater detail in the examples provided hereinafter.

III. Uses of Monoclonal Antibodies

The monoclonal antibodies of the present invention, immunoreactive fragments or recombinants thereof, can be used either alone, or in combination with other antibodies, in: (1) in vitro diagnostic assays using labeled monoclonal antibodies for the detection of the D612-reactive antigen in body fluids of patients; (2) in vivo diagnostic assays (diagnostic imaging or use with an intraoperative hand held gamma detecting probe) using monoclonal antibodies, of the present invention, immunoreactive fragments or recombinants thereof, conjugated to an imaging marker, for the in situ detection of colorectal carcinoma lesions, (3) in vivo cancer treatment using monoclonal antibodies of the present invention, immunoreactive fragments or recombinants thereof alone or conjugated to a therapeutic agent such as a radionuclide, drug, toxin, other antibodies, or used with effector cells or via a complement reaction mechanism; (4) immunohistopathology or immunocytochemistry for the detection or phenotyping of carcinoma cells; and (5) as immunogen to activate the anti-idiotype network for active immunotherapy against carcinomas.

A. In Vitro Diagnostic Assays

In vitro diagnostic assays for detection of primary human carcinomas or metastases therefrom by detecting the reactive antigen in body fluids of patients using the monoclonal antibodies of the present invention, immunoreactive fragments or recombinants thereof are described in greater detail below.

The body fluid obtained from a patient is contacted with monoclonal antibodies of the present invention, immunoreactive fragments or recombinants thereof. A diagnosis is then made by determining the amount of monoclonal antibody, immunoreactive fragment or recombinant thereof binding to substances present in the body fluid and comparing the amount of monoclonal antibody bound to the body fluid substances to a predetermined base level as hereinafter defined. The detection of bound monoclonal antibodies exceeding the base level indicates the presence of a human colorectal carcinoma or metastases therefrom.

Any body fluids suspected of containing the reactive antigen, such as blood (serum or plasma), sputum, ascites fluids, pleural effusions, urine and/or biopsy specimens can be used for in vitro diagnostic methods. Serum or plasma are the more preferred body fluids for use in the practice of the invention.

The amount of antibody bound to substances in the body fluid can be determined by means of immunochemical assays by means such as those described, for example, in Klug, T. L. et al, *Cancer Res.* 44:1048–1053 (1984); Klug, T. L. et al, *Int. J. Cancer* 38:661–669 (1986), Herlyn, M. et al, *J. Clin. Immunol.* 2:135–140 (1982), Metzgar, R. S. et al, *Proc. Natl. Acad. Sci., USA* 81:5242–5246 (1984), Papsidero, L. D. et al, *Cancer Res.* 44:4653–4657 (1984), Hayes, D. F. et al, *J. Clin. Invest.* 75:1671–1678 (1985), Killian, C. S. et al, *Cancer Res.* 45:886–891 (1985), Hedin, A et al, *Proc. Natl. Acad. Sci., USA* 80:3470–3474 (1983), Pekary, A. E. et al, *Clin. Chem.* 30:1213–1215 (1984), Bast, R. C. et al, *New England J. Med.* 309:883–887 (1983) and Bellet, D. H. et al, *Proc. Natl. Acad. Sci., USA* 81:3869–3873 (1984), the disclosures of all of which are specifically incorporated herein by reference.

B. In Vivo Diagnostic Assays

In vivo diagnostic assays for detection of human gastrointestinal carcinomas or metastases therefrom using the monoclonal antibodies of the present invention, are described in more detail below.

Monoclonal antibodies of the present invention, including immunoreactive fragments or recombinants thereof and an imaging marker are administered to a patient. The marker may be conjugated to the antibody before administration. Alternatively, subsequent administration of the marker or linker conjugated marker after administration of the monoclonal antibody is acceptable. The presence of the imaging marker in the patient is detected by exposing the patient to an appropriate means for detecting the particular marker.

Administration and detection of the antibody-imaging marker conjugate as well as methods of conjugation of the antibody to the imaging marker are accomplished by methods known to those skilled in the art, as described, for example, in Goldenberg, D. M. et al, *New England J. Med.* 298-1384–1388 (1978); Goldenberg, D. M. et al, *J. A. M. A.* 250:630–635 (1983); Goldenberg, D. M. et al, *Gastroenterol.* 84:524–532 (1983); Siccardi, A. G. et al *Cancer Res.* 46:4817–4822 (1986); Epenetos, A. A. et al, *Cancer* 55:984–987 (1985); Philben, V. J. et al, *Cancer* 57:571–576 (1986); Chiou, R. et al, *Cancer Res.* 45:6140–6146 (1985); Hwang, K. M. et al, *J. Natl. Cancer Inst.* 76:849–855 (1986); Colcher, D. et al, *Cancer Res.* 43:736–742 (1983); Colcher, D. et al, *Laboratory Research Methods in Biology and Medicine Immunodiagnostics*, New York, Alan R. Liss, pp. 215–258 (1983); Keenan, A. M. et al, *J. Nucl. Med.* 25:1197–1203 (1984); Colcher D. et al, *Cancer Res.* 47:1185–1189 (1987); Esteban, J. M. et al., *Intl. J. Cancer* 39:50–59 (1987); Martin, D. T., et al, *Curr. Surg.* 41:193–194 (1984); Martin, E. W. Jr. et al, *Hybridoma* 5:S97–S108 (1986); and Martin, D. T. et al, *Am. J. Surg.* 150:672–675 (1985); the disclosures of all of which are specifically incorporated herein by reference.

The dosage will vary depending upon the age and weight of the patient, but generally a one time dosage of about 0.1 to 20 milligrams of antibody-marker conjugate is sufficient. A more preferred dosage is about 1.0 to 2.0 milligrams of antibody-marker conjugate.

Imaging markers which can be conjugated to the antibody are known to those skilled in the art and include substances which can be detected by a gamma scanner or hand held gamma probe, Positron Emission Tomography or the like as described in the references cited above and substances which can be detected by nuclear magnetic resonance imaging using a nuclear magnetic resonance spectrometer (also described in the references cited above).

Suitable examples of substances which can be detected using a gamma scanner or the like include $^{125}I$, $^{131}I$, $^{123}I$, $^{111}In$, and $^{99m}Tc$. $^{111}In$ and $^{99m}Tc$ are preferred due to their low energy and suitability for long range detection.

An example of a substance which can be detected using a nuclear magnetic resonance spectrometer or the like is the nuclear magnetic spin-resonance isotope gadolinium (Gd).

C. In Vivo Treatment

In vivo treatment of human gastrointestinal carcinomas or metastases therefrom using monoclonal antibodies of the present invention, immunoreactive fragments or recombinants thereof is described in greater detail below.

A pharmaceutically effective amount of monoclonal antibodies of the present invention, immunoreactive fragments or recombinants thereof unconjugated or conjugated to a therapeutic agent is administered to a patient.

Methods of preparing and administering the monoclonal antibody-therapeutic agent conjugate as well as suitable dosages will depend on the age and weight of the patient and the therapeutic agent employed and are known to or readily determined by those skilled in the art. Representative protocols are described in the references cited below.

Examples of the monoclonal antibody-therapeutic agent conjugates which can be used in therapy include antibodies coupled to radionuclides, such as $^{131}$I, $^{90}$Y, $^{105}$Rh, $^{47}$Sc, $^{67}$Cu, $^{212}$Bi, and $^{211}$At, as described, for example in Goldenberg, D. M. et al, *Cancer Res.* 41:4354–4360 (1981); Carrasquillo, J. A. et al, *Cancer Treat. Rep.* 68:317–328 (1984); Zalcberg, J. R. et al, *J. Natl. Cancer Inst.* 72:697–704 (1984); Jones, D. H. et al, *Int. J. Cancer* 35:715–720 (1985); Lange, P. H. et al, *Surgery* 98:143–150 (1985); Kaltovich, F. A. et al, *J. Nucl. Med.* 27:897 (1986), Order, S. E. et al., *Int. J. Radiother. Oncol. Biol. Phys.* 8:259–261 (1982), Courtenay-Luck, N. et al, *Lancet* 1:1441–1443 (1984) and Ettinger, D. S. et al, *Cancer Treat. Rep.* 66:289–297 (1982), the disclosure of all of which are specifically incorporated herein by reference; antibodies coupled to drugs or biological response modifiers such as methotrexate, adriamycin, and interferon as described, for example, in Chabner, B. et al, *Cancer, Principles and Practice of Oncology*, Philadelphia, Pa., J. B. Lippincott Co. Vol. 1, pp. 290–328 (1985); Oldham, R. K. et al, *Cancer, Principles and Practice of Oncology*, Philadelphia, Pa. J. B. Lippincott Co., Vol. 2, pp. 2223–2245 (1985); Deguchi, T. et al, *Cancer Res.* 46:3751–3755 (1986); Deguchi, T. et al, *Fed. Proc.* 44:1684(1985); Embleton, M. J. et al, *Br. J. Cancer* 49:559–565 (1984) and Pimm, M. V. et al, *Cancer Immunol. Immunother.* 12:125–134 (1982), the disclosure of all of which are specifically incorporated herein by reference; antibodies coupled to toxins, as described, for example, in Uhr, J. W. et al, *Monoclonal Antibodies and Cancer*, Academic Press, Inc., pp. 85–98 (1983), Vitetta, E. S. et al, *Biotechnology and Bio. Frontiers*, Ed. P. H. Abelson, pp. 73–85 (1984) and Vitetta, E. S. et al, *Science* 219:644–650 (1983), the disclosure of all of which are specifically incorporated herein by reference; heterobifunctional antibodies for example, antibodies coupled or combined with another antibody so that the complex binds both to the carcinoma and effector cells, e.g., killer cells such as lymphokine activated killer (hereinafter "LAK") (see Rosenberg, S. A. et al, *Science* 223:1412–1415 (1984)) or T cells, as described, for example, in Perez, P. et al, *J. Exper. Med.* 163:166–178 (1986); and Lau, M. A. et al, *Proc. Natl. Acad. Sci. USA* 82:8648–8652 (1985); the disclosures of both of which are specifically incorporated herein by reference; and native, i.e., non-conjugated or non-complexed, antibody, as described in, for example, in Shiloni, E. et al, *J. Immunol.* 138:1992–1998 (1987); Eisenthal, A. et al, *Cancer Res.* 47:2771–2776 (1987); Honsik, C. J. et al, *Pro. Natl. Acad. Sci. USA* 83:7893–7897; Herlyn, D. et al, *Proc. Natl. Acad. Sci. USA* 79:4761–4765 (1982); Schulz, G. et al, *Proc. Natl. Acad. Sci. USA* 80:5407–5411 (1983); Capone, P. M. et al, *Proc. Natl. Acad. Sci. USA* 80:Z328–7332 (1983); Sears, H. F. et al, *Cancer Res.* 45:5910–5913 (1985); Nepom, G. T. et al, *Proc. Natl. Acad. Sci. USA* 81:2864–2867 (1984); Koprowski, H. et al, *Proc., Natl. Acad. Sci. USA* 81:216–219 (1984); and Houghton, A. N. et al, *Proc. Natl. Acad. Sci. USA* 82:1242–1246 (1985) all of which are specifically incorporated herein by reference.

The monoclonal antibody-therapeutic agent conjugate is delivered to the gastrointestinal carcinoma site where binding occurs, thereby directly exposing the carcinoma tissue to the therapeutic agent. The unconjugated monoclonal antibodies can be administered in the presence of lymphokines such as interleukin-2 (see Rosenberg, S. A. et al, *Science* 223:1412–1415 (1984)) to enhance the therapeutic potential of the effector cells. Previous therapeutic studies using high doses of monoclonal antibodies such as 17-1A, which is reactive with normal gastrointestinal epithelium, have resulted in no apparent toxicity (see Sears, H. F. et al, *J. Biol. Resp. Mod.* 3:138–150 (1984)). Furthermore, even where toxicity results in damage, normal gastrointestinal epithelium has been shown to regenerate after such exposure while carcinoma cells do not regenerate.

D. Immunohistochemistry and Immunocytochemistry Assays

Immunohistochemistry (hereinafter "IHC") and Immunocytochemistry (hereinafter "ICC") assays for the diagnosis of human carcinomas or metastases therefrom using the monoclonal antibodies of the present invention, are carried out as described below.

The monoclonal antibodies of the present invention, are added to a slide containing a 5 micron section of a biopsy specimen (for IHC) or cells (for ICC) from body fluid (such as a pleural effusion, ascites sputum, or vaginal fluid). A series of linkers (e.g., biotinylated horse anti-mouse IgG followed by avidin DH:biotinylated horseradish peroxidase complex) and dyes (e.g. diaminobenzidine) are then added to the slides to detect binding of the monoclonal antibody, immunoreactive fragment or recombinant thereof to carcinoma cells in the biopsy or body fluid by a color reaction, i.e., carcinoma cells will look reddish-brown while normal and benign cells will look blue (the background stain). Alternate linkers, dyes, and subsequent color reactions, may be used (see, for example, Sternberger, L. A. *Immunocytochemistry*, New York, John Wiley & Sons, Second Edition pp. 82–169 (1979)). By this method: (a) carcinoma cells can be detected in biopsy specimens and body fluids as an adjunct to making a diagnosis of cancer, and (b) a differential diagnosis can be made; for example, D612 has been shown to bind gastrointestinal adenocarcinoma and not other carcinomas. Thus, detection of binding of monoclonal antibodies of the present invention (immunoreactive fragments or recombinants thereof) would indicate a gastrointestinal origin of the primary carcinoma.

The use of IHC and ICC assays for the diagnosis of cancer or to make differential diagnoses are accomplished by methods known in the art, as described, for example, in Nuti, M. et al, *Intl. J. Cancer* 29:539–545 (1982), Stramignoni, D. et al., *Intl. J. Cancer* 31:543–552 (1983), Szpak, C. A. et al., *Acta Cytologica* 28:356–367 (1984), Johnston, W. W. et al., *Cancer Res.* 45:1894–1900 (1985), Szpak, C. A. et al., *Am. J. Path.* 122:252–260 (1986), Thor, A. et al., *J. Natl. Cancer Inst.* 76:995–1006 (1986), Martin, S. E. et al, *Am. J. Clin. Path.* 86:10–18 (1986), Nuti, M. et al., *Intl. J. Cancer* 37:493–498 (1986), Johnson, V. G. et al., *Cancer Res.* 46:850–857 (1986), Thor, A. et al, *Cancer Res.* 46:3118–3124 (1986), Ohuchi, N. et al., *Intl. J. Cancer* 38:643–650 (1986), Johnston, W. W. et al, *Cancer Res.* 46:6462–6470 (1986), and Thor, A. et al, *Cancer Res.* 47:505–512 (1987), the disclosures of all of which are specifically incorporated herein by reference.

The amount of any monoclonal antibody of the present invention, used per slide and the incubation time and temperature may vary, but generally, the IHC and ICC assays are conducted at room temperature for 30 minutes using about 20 micrograms per ml of monoclonal antibody.

E. Activating the Anti-Idiotype Network

Activating the anti-idiotypic network for cancer therapy using monoclonal antibodies of the present invention (including immunoreactive fragments or recombinants thereof) are carried out as described.

Monoclonal antibodies of the present invention, immunoreactive fragments or recombinants thereof (designated Ab 1) are administered to a patient at intervals. The immune system of the patient will respond by the generation of antibodies (designated Ab 2) which have binding specificity to the binding site of Ab 1. These anti-idiotype antibodies (Ab 2's) will then elicit the formation of antibodies (designated Ab 3) which have binding specificity for the binding site of Ab 2. The Ab 2 antibodies will be an internal image of the original reactive antigen, and thus the Ab 3 antibodies will have binding specificity and potentially destroy a carcinoma producing the D612-reactive antigen.

The use of monoclonal antibodies to activate the idiotypic network and the procedures used to accomplish this are readily known to those skilled in the art. (See, for example, Ninsonoff, A. et al, *Clin. Immunol. and Path.* 21:397–406 (1981), Forstrom, J. W. et al, *Nature* 303:627–629 (1983), Kauffman, R. S. et al, *J. Immunol.* 131:2539–2541 (1983); Reagen, K. J. et al, *J. Virol.* 48:660–666 (1983); Koprowski, H. et al, *Pro. Natl. Acad. Sci. USA* 81:216–219 (1984), Herlyn, D. et al, *J. Immunol.* 143:1300–1304 (1985), Koprowski, H. et al, *J. Immunol. Meth.* 85:27–38 (1985), Koprowski, H. et al, *Science* 232:100–102 (1985), Greene, M. I. et al, *J. Immunol.* 137:2930–2936 (1986), Kohler, H. et al, *J. Immunol.* 137:1743–1749 (1986), Notkins, A. L. et al, *J. Exp. Med.* 163:1355–1360 (1986), the disclosures of all of which are specifically incorporated herein by reference).

The activation of the anti-idiotypic network can be used to stimulate a patient's immune system so that the patient can mount an active immune response against carcinomas producing the D612-reactive antigen.

The following examples are provided for illustrative purposes only and are in no way intended to limit the scope of the present invention.

EXAMPLE 1

Preparation of Monoclonal Antibodies

A. Preparation of Immunogen and Cell Extracts

The biopsy specimen used as immunogen was finely minced prior to extraction. The sample was diluted with 10 mM Tris-HCl (250 mM Tris:HCl:176 mM:NaC$_2$H$_3$O$_2$:250 mM NaCl) pH 7.2 (Bethesda Research Laboratories, Gaithersburg, Md.) (hereinafter "Tris-HCl") containing 0.2 mM CaCl$_2$ and homogenized using a Silverson homogenizer for 2 minutes at top speed, and then subjected to nitrogen cavitation using a cell disruption bomb (Parr Instrument Co., Moline, Ill.) for 5 minutes at 1000 pounds per square inch. The sample was then clarified by centrifugation for 10 minutes at 1,000×g. To obtain membrane enriched fractions, the supernatant fluid was layered over a discontinuous 20–40% sucrose gradient (10 mls each) in 10 mM Tris-HCl (pH 7.2) containing 2 mM CaCl$_2$. After centrifugation at 90,000×g for 17 hours the membrane enriched fraction was removed from the interface of the 20–40% sucrose. This fraction was diluted with 10 mM Tris-HCl (pH 7.2), pelleted at 90,000×g for 1 hour, and resuspended in phosphate buffered saline, 80 mM Na$_2$HPO$_4$: 1.5 mM KH$_2$PO$_4$:2.5 mM KCl:140 mM NaCL:0.5 mM MgCl$_2$:1.0 mM CaCl$_2$, pH 7.2 (Grand Island Biological Co., Grand Island, N.Y.) (hereinafter "PBS"). The membrane enriched fraction was then sonicated for 1 minute at the maximum setting (Heat Systems Ultrasonics, Plainview, N.Y.). The protein concentration was then determined by the method of Lowry, O. et al, *J. Biol. Chem.* 193: 265–275 (1951). Samples were aliquoted and stored at −20° C. for further use. Extracts of biopsies and tissue culture cells were prepared in the same manner as the immunogen with the exception that the 20–40% sucrose gradient step (i.e., the preparation of membrane enriched fractions) indicated above was omitted and the extracts were centrifuged after sonication at 10,000×g for 10 minutes. Monolayer tissue culture cells were removed prior to extractions by scraping and were washed extensively in PBS.

B. Immunizations and Hybridoma Methodology

Four week old BALB/c mice were immunized by intraperitoneal (hereinafter "i.p.") injection of 100 micrograms of a membrane-enriched fraction of a moderately differentiated primary colon adenocarcinoma emulsified in an equal volume of complete Freund's adjuvant. Seven days later mice were given an additional i.p. inoculation of 100 micrograms of immunogen emulsified in an equal volume of incomplete Freund's adjuvant. After an additional seven days, mice were boosted intravenously (hereinafter "i.v.") with 10 micrograms of immunogen. Spleens were asceptically removed for fusion three days later.

C. Preparation of Hybridomas

Somatic cell hybrids (hybridomas) were prepared using a modification of the method of Herzenberg, L.A. et al, *Handbook of Experimental Immunology*, Oxford, Blackwell pp. 25.1–25.7 (1978). More specifically, single cell suspensions of spleen cells from the immunized mice were made by passing the spleen tissue of the mice through a No. 3 mesh stainless steel screen (B. Fenenco Co., Inc., Norcester, Mass.). The spleen cells and NS-1 mouse myeloma cells (ATCC No. TIB 18) were washed in RPMI-1640 medium, containing 2.0 mM glutamine, 1.0 mM sodium pyruvate, 50 units/ml pencillin, 50 micrograms/ml streptomycin and 0.25 micrograms/ml Fungizone, an antimycotic mixture (Grand Island Biological Company, Grand Island, N.Y.). Then, the spleen cells and NS-1 mouse myeloma cells were mixed at a 4:1 ratio, and fused with 50% (v/v) polyethylene glycol (M.W. 1500) (BDH Chemical Ltd., Poole, England). After fusion, individual wells of 96-well microtiter plates (Costar, Cambridge, Mass.) were seeded with 1×10$^6$ total cells (0.1 ml) of the cell suspension. Fused cells were then selected for growth with HAT media.

Cloning of hybridoma cell lines was performed by limiting dilution. Specifically, twenty-four wells of a 96-well microtiter plate (Costar, Cambridge, Mass.) were seeded with one of the following concentrations of hybridoma cells: 10 cells/well, 5 cells/well, or 0.5 cell/well. Mouse thymocytes, derived from the thymus glands of four-week old Balb/c mice, were added to each well as feeder cells at a concentration of 10$^6$ cells/well. Wells were seeded at the concentration that eventually resulted in the growth of single cell cultures.

A total of 1,377 initial hybridoma cultures were obtained. Hybridoma cell lines selected for further screening were cloned twice.

D. Solid Phase Radioimmunoassays

Hybridoma tissue culture supernatants were assayed for specific antibody production in SPRIA using cell extracts from different colon carcinomas, normal tissues and partially purified preparations of carcinoembryonic antigen (hereinafter "CEA") and tumor associated glycoprotein-72 (hereinafter "TAG-72"). Purified TAG-72 (14 units) (see Johnson, V.G. et al, *Cancer Res.* 46: 850–857 (1986)), or purified CEA (20 nanograms), or cell extract (5 micrograms) were added to each well of a 96-well polyvinyl microtiter plate and allowed to dry overnight at 37° C. in a non-humidified incubator. The wells were quenched to minimize nonspecific protein binding by the addition of 100 microliters of 5% bovine serum albumin (hereinafter "BSA") in PBS containing $Ca^{+2}$ and $Mg^{+2}$. The BSA solution was aspirated after a 1 hour incubation at 37° C. Tissue culture supernatant (50 microliters) were added to each well and incubated for 1 hour at 37° C.; the unbound Ig was removed and the plates were washed with PBS 1% BSA. Each well was then incubated for 1 hour at 37° C. with $^{125}I$-labeled goat anti-mouse IgG (75,000 cpm in 25 microliters; Kirkegaard and Perry, Gaithersburg, Md.). The unbound $^{125}I$-goat anti-murine IgG was aspirated, and the wells were extensively washed with PBS 1% BSA. The wells were then subjected to autoradiography using Kodak XAR X-ray film and DuPont Lightning Plus intensifying screens. The films were developed after overnight exposure at −70° C. The bound radioactivity was also detected by cutting and counting the individual wells in a gamma scintillation counter.

The reactivity of MAb D612 with extracts of biopsies of neoplastic tissues and extracts of neoplastic cell lines is shown in Table 1. Neoplastic and normal adult tissues were obtained from the Department of Surgery and Pathology, George Washington University, Washington, D.C., and from the Regina Elena Cancer Institute, Rome, Italy. The BALB/c non-secreting myeloma cell line, P3-NS1-Ag4-1 (NS-1) (ATCC No. TIB 18) was obtained from Dr. J. Kim, NIH, Bethesda, Md. The LS-174T (ATCC No. CL 188) and WiDr (ATCC No. CCL 218) colon adenocarcinoma cell lines were obtained from the American Type Tissue Culture Collection, Rockville, Md. The HT-29 (ATCC No. HTB 39) colon carcinoma cell line and the breast carcinoma cell lines MCF-7 (ATCC No. HTB 2) and BT-20 (ATCC No. HTB 19) were obtained from the Breast Cancer Task Force, NCI, NIH, Bethesda, Md. The A204 rhabdomyosarcoma cell line (ATCC No. HTB 82), the A375 melanoma cell line (ATCC No. CRL 1619) and bladder carcinoma cell lines HA-698 and HA-1054 were obtained from Dr. S. Aaronson, NCI, NIH, Bethesda, Md. Other cell lines used were: Colo 320 DM (ATCC No. CCL 220), Colo 320 HSR (ATCC No. CCL 220.1) DLD 1 (ATCC No. CCL 221), CBS and GEO (see Brattain, M.G. et al, *Oncodev. Biol. Med.* 2: 355–366 (1981)), VACO 6 (see McBain, J.A. et al, *Cancer Res.* 44: 5813–5821 (1984)), MIP (see Niles, R.M. et al, *Cancer Invest.* 5: 545–552 (1987)), HSO578T (ATCC No. HTB 126), ZR 75-1 (ATCC No. CRL 1500), MDA-MB 231 (ATCC No. HTB 26), T24 (ATCC No. HTB 4), A427 (ATCC No. HTB 53), and OVCAR-3 (ATCC No. HTB 161). Lines M35Lu, M36Lu and M39Hep were obtained from Dr. P. Noguchi. M35Lu and M36Lu are metastases to the lung and M39Hep is a metastasis to the liver derived from a colon carcinoma cell line HT29 grown in nude mice. CBS and GEO were obtained from Dr. M. Brattain, Baylor College of Medicine, Houston, Tex., DLD 1 and MIP were obtained from Dr. P. Thomas, New England Deaconess Hospital, Boston, Mass., VACO 6 was obtained from Dr. J. Willson, University Hospital of Cleveland, Cleveland, Ohio. and the Flow 4000 line was obtained from Flow Laboratories, Inc., Rockville, Md. All cell lines were maintained on the growth medium recommended by their respective sources. The SPRIAs employed showed three of five colon carcinoma biopsies and six of thirteen colon carcinoma cell lines reactive with monoclonal antibody D612. However, none of seven breast carcinoma biopsies, five breast carcinoma cell lines or seven cell lines of other cancers as well as normal human fibroblasts showed any reactivity with monoclonal antibody D612, see Table 1.

TABLE 1

Reactivity of Monoclonal Antibody D612 with Extracts of Biopsies of Neoplastic Tissues and Cell Lines

| | cpm bound |
|---|---|
| Colon Carcinoma: Biopsy | |
| 1 (primary, immunogen) | 2,627 |
| 2 (primary) | neg[a] |
| 3 (primary) | neg |
| 4 (primary) | 2,981 |
| 5 (metastatic) | 2,298 |
| Colon Carcinoma: Cell Lines | |
| Experiment 1 | |
| LS-174T | 4,165 |
| HT-29 | neg |
| M36Lu | 4,458 |
| M35Lu | neg |
| M39Hep | 795 |
| WiDr | neg |
| Colo 320 DM | neg |
| Colo 320 HSR | neg |
| Experiment 2 | |
| LS-174T[b] | 6,084 |
| CBS[b] | 15,866 |
| VACO 6[c] | 2,581 |
| GEO[c] | 16,927 |
| DLD 1[b] | neg |
| MIP[b] | neg |
| Breast Carcinoma: Biopsy | |
| Primary (n = 5) | neg |
| Metastatic (n = 2) | neg |
| Breast Carcinoma: Cell Lines | |
| MCF-7 | neg |
| BT-20 | neg |
| HSO578T | neg |
| ZR 75-1 | neg |
| MDA-MB 231 | neg |
| Bladder Carcinoma: Cell Lines | |
| T24 | neg |
| HA 1054 | neg |
| HA 698 | neg |
| Lung Carcinoma | |
| A427 | neg |
| Melanoma | |
| A375 | neg |
| Rhabdomyosarcoma | |
| A204 | |
| Normal Human Fibroblast | |
| Flow 4000[c] | neg |

D612 tissue culture supernatant was used unless otherwise specified. 500 cpm were subtracted from all values since approximately that value was observed with NS-1 tissue culture supernatant.
[a]neg = less than 500 cpm;
[b]purified IgG, 1 microgram per well was used;
[c]purified IgG, 0.5 micrograms per well was used.

A variety of extracts from normal human adult tissues were also analyzed for reactivity with D612. As seen in Table 2, all five normal colon biopsies expressed the D612-reactive antigen, whereas no reactive antigen was detected in extracts of the various normal tissues listed.

TABLE 2

Reactivity of Monoclonal Antibody D612 with Extracts of Normal Human Tissues

| Tissue | cpm bound |
|---|---|
| Colon | |
| 1 | 2,597 |
| 2 | 4,002 |
| 3 | 2,441 |
| 4 | 3,293 |
| 5 | 1,645 |
| Spleen (n = 4) | neg |
| Liver (n = 3) | neg |
| Kidney (n = 2) | neg |
| Lung (M 413)[b] | neg |
| RBC (11 preparations)[c] | neg |
| PMN[d] | neg |
| Lymphocytes (2 preparations) | neg |
| Lymphoblast (NC-37) | neg |
| Fetal Lung (WI-38)[b] | neg |

[a]500 cpm were subtracted from all values since approximately that value was observed with NS-1 (ATCC No. TIB 18) tissue culture supernatant;
[b]cell line;
[c]red blood cells, 11 separate preparations tested individually;
[d]PMN = Polymorphonuclear leukocytes.

To rule out the possibility that D612 is reactive with other colon carcinoma associated antigens, five preparations of CEA and purified TAG-72 were analyzed. As can be seen in Table 3, D612 showed only weak reactivity to one of five CEA preparations (most probably due to a minor contamination of that preparation) and no reactivity to TAG-72.

Studies were also conducted to determine if the antigen detected by D612 is shed. Previous studies have shown that the antigen detected by monoclonal antibody CAA (see Muraro, R. et al, Int. J. Cancer 39: 34-44 (1987)) is shed into supernatant fluids of tumor cell cultures and thus this antibody served as a suitable control. The antigens detected by monoclonal antibodies D612 and CAA were readily detected in extracts of the LS-174T human colon cancer cell line (ATCC No. CRL 188). In contrast, the antigen detected by monoclonal antibody CAA was readily detected in the serum free supernatant medium of these cultures, whereas the antigen detected by monoclonal antibody D612 was barely detectable, if at all.

TABLE 3

Reactivity in Solid Phase RIA of Monoclonal Antibody D612 with Purified Antigens[a]

| MAb | CEA Preparations | | | | | TAG-72 |
| | 1 | 2 | 3 | 4 | 5 | |
|---|---|---|---|---|---|---|
| COL-1[b] | 23,362[c] | 19,316 | 12,429 | 23,773 | 24,448 | neg[d] |
| B72.3[e] | neg | neg | neg | neg | neg | 2,386 |
| Anti-CAA | 3,512 | neg | 3,246 | neg | neg | neg |
| D612 | 2,108 | neg | neg | neg | neg | neg |

[a]500 cpm were subtracted from all values since approximately that value was observed with NS-1 tissue culture supernatant;
[b]anti-CEA monoclonal antibody;
[c]cpm bound;
[d]tested in another assay;
[e]anti-TAG-72 monoclonal antibody.

EXAMPLE 2

Isotyping Assay

Fifty microliters of polyclonal anti-mouse IgG (Jackson Immunoresearch Laboratories, Inc., West Grove, Pa.) was absorbed onto a 96-well polyvinyl chloride (Dynatech Laboratories, Alexandria, Va.) microtiter plate. The IgG was diluted with PBS. The plates were incubated overnight at 37° C. The following day, 100 microliters of 5.0% (w/v) BSA in PBS was added to each well and allowed to incubate for 1 hour to minimize non-specific absorption. The wells were then washed with 1.0% (w/v) BSA in PBS. Fifty microliters of undiluted D612 culture supernatant was added to each of two wells. The plates were again incubated for 1 hour at 37° C. after which time they were washed 3 times with 1.0% (w/v) BSA in PBS. Rabbit-anti-mouse $IgG_1$, $IgG_{2a}$, $IgG_{2b}$, $IgG_3$, IgM, IgA (Cooper Biomedical, Malvern, Pa.) DC-12 (NIH, NCI, LTIB) and control 1.0% (w/v) BSA in PBS were added at 50 microliters per well. Following a 1 hour incubation, the plates were washed 3 times as described above. Then 50,000 cpm of $^{125}$I-labeled Protein A (SPA) (Staphylococcus Protein A, Pharmacia, Piscataway, N.J.) were added to each well, incubated for 1 hour, washed 4 times with 1.0% (w/v) BSA in PBS and the cpm per well was counted in a gamma counter. The results demostrated that the isotype of monoclonal antibody D612 is $IgG_{2a}$.

EXAMPLE 3

Purification of Immunoglobulin

D612 IgG was purified from ascitic fluid by ammonium sulfate precipitation followed by ion-exchange chromatography using WAX column (DuPont, Wilmington, Del.). The antibody was eluted by a 0 to 500 mM NaCl gradient in 20 mM Tris—HCl (pH 7.0). Column fractions were analyzed by sodium dodecyl sulfate-polyacrylamide gel electrophoresis (hereinafter "SDS-PAGE") and appropriate fractions, with purity of over 90% of the protein being IgG, were pooled and dialyzed against PBS. The concentration was determined by the method of Lowry, O. et al, J. Biol. Chem. 193:265-275 (1951) using a BSA standard.

EXAMPLE 4

Western Blotting

Forty micrograms of cell extracts diluted in SDS-PAGE sample buffer (0.125M Tris—HCl [pH 6.8]4% SDS, 20% glycerol, 10% 2-mercaptoethanol), were loaded onto a 5-20% linear gradient SDS-PAGE. After electrophoresis, proteins were transferred to nitrocellulose paper (0.45 um pore size) at 4° C. for 4 hours at 30V in transfer buffer (25 mM Tris—HCl [pH 8.3]192 mM glycine, 20% methanol). The nitrocellulose sheets were then incubated in PBS containing 5% BSA for 2 hours at room temperature and washed in PBS with 0.05% Tween-20. Ten ml of hybridoma tissue culture supernatant were added; incubation continued for 1 hour at room temperature with gentle agitation. After washing with PBS with 0.05% Tween-20, the blots were incubated for 1 hour at room temperature with $^{125}$I-labeled goat anti-murine IgG. The unbound second antibody was removed by several washes with PBS with 0.05% Tween-20. The blotted filters were then exposed to Kodak XAR X-ray film with a DuPont Lightning Plus intensifying screen at −70° C. For all the experiments NS-1 (ATCC No. TIB 18) tissue culture supernatant was used as a negative control.

Figure 1:
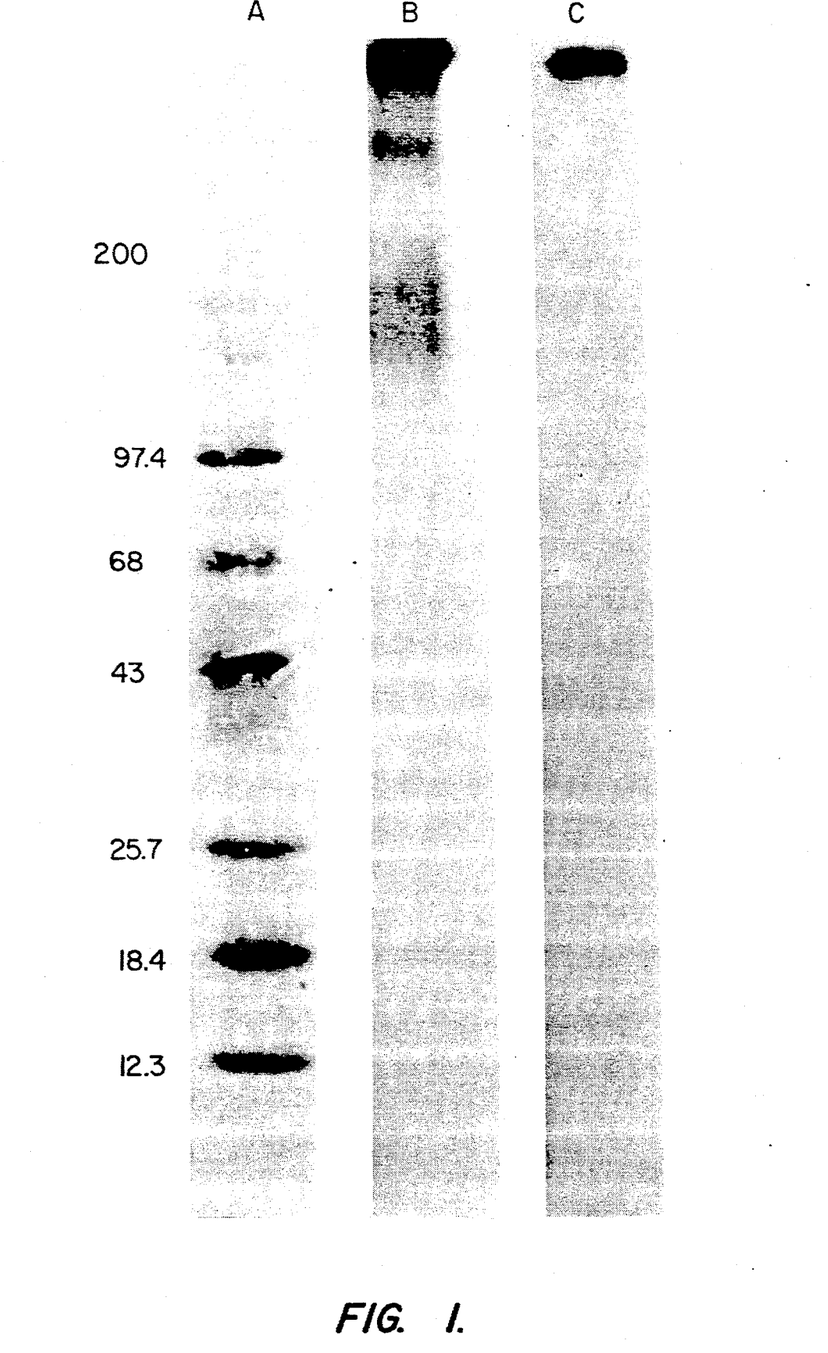
FIG. 1 is an immunoblot analysis of a human colon carcinoma extract. An extract of the LS-174T human colon carcinoma cell line (ATCC No. CRL 188) was subjected to electrophoresis and blotting as described in Example 4. The filters were incubated with hybridoma tissue culture fluids of anti-CAA (Lane B) and D612 (Lane C). The bands were detected using $^{125}$goat anti-mouse IgG and autoradiography. Markers are shown in Lane A in units of kd$\times 10^3$.

As shown in FIG. 1, Western blot analyses demonstrated a high molecular weight D612 reactive antigen with an apparent molecular weight of ≧$10^6$ daltons.

This is contrasted with the epitopes detected by the colon associated antigen detected by monoclonal antibody CAA. It is also clear from the Western blot that D612 does not react with the 180,000 d glycoprotein characteristic of anti-CEA monoclonal antibodies or the lower molecular weight forms detected by members of the CEA-related family. While the Western blot of D612 is similar to that seen with monoclonal antibody B72.3 (U.S. Pat. No. 4,612,282), it is shown in Table 2 that D612 does not react with the B72.3 reactive antigen, TAG-72. Moreover, its biologic distribution is quite distinct from that of B72.3.

EXAMPLE 5

Cell Surface Reactivity

To determine if D612 is reactive with an epitope expressed on the cell surface, six colon adenocarcinoma cell lines were reacted in live cell radioimmunoassays (hereinafter "RIAs") for cell surface reactivity. As can be seen in Table 4, D612 was strongly reactive with three colon carcinoma cell lines, whereas showed no significant level of binding to three other colon tumor lines. D612 also showed no binding to the cell surface of the OVCAR-3 and A375 lines (Table 4) the human embryonic cell lines WI-38 (ATCC No. CCL 75) and MRC-5 (ATCC No. CCL 171).

Figure 2:
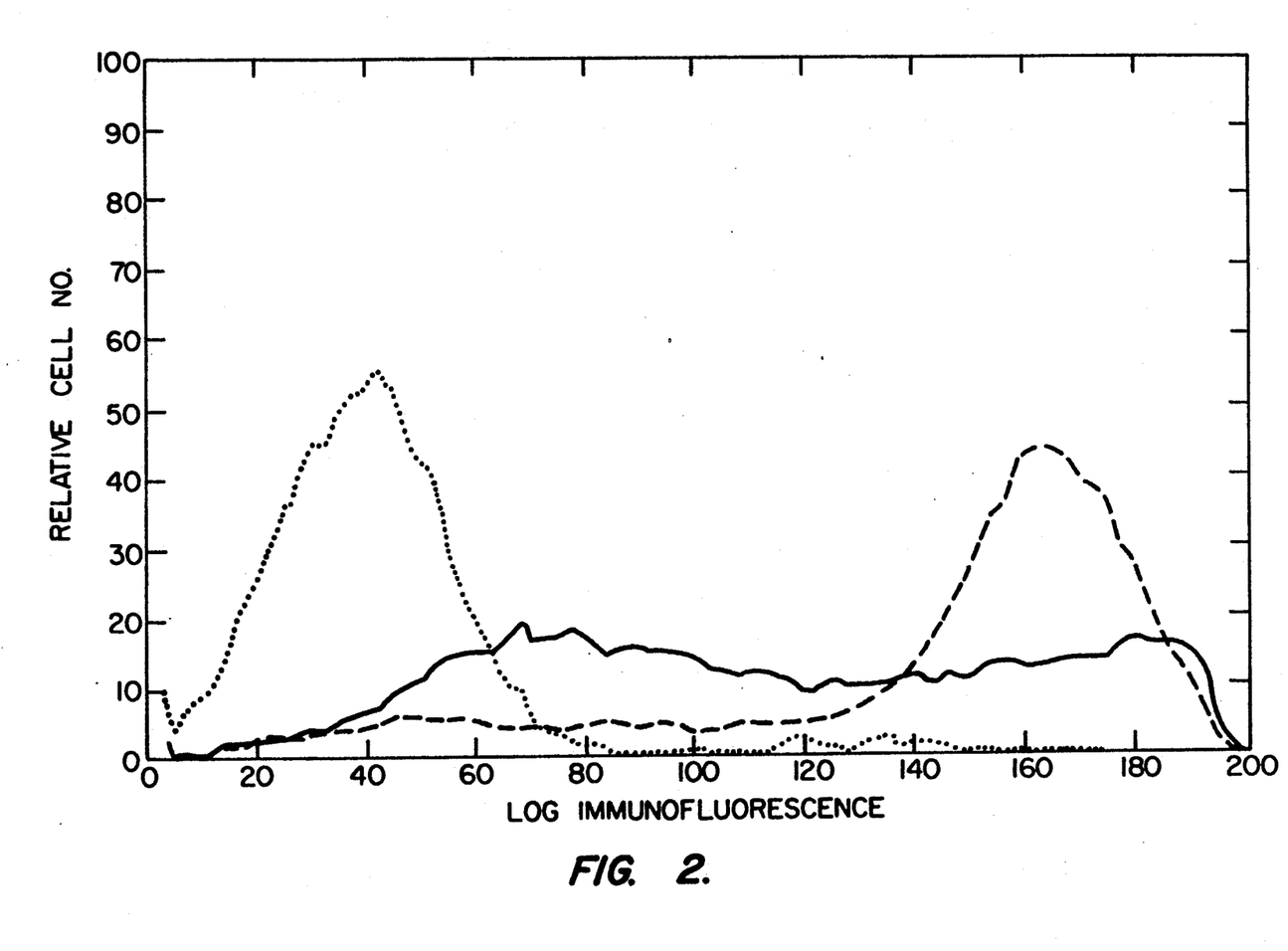
FIG. 2 is a cell sorter analysis of the binding of the D612 (- - -) and CAA (—) monoclonal antibodies for the LS-174T human colon carcinoma cell line (ATCC No. CRL 188). The dotted line (. . . ) represents the sorter analysis in the presence of either no antibody or an irrelevant monoclonal antibody, MOPC-21 (Organon Technika, West Chester, Pa.).

Fluorescence activated cell sorter (hereinafter "FACS) analysis of monoclonal antibody D612 with the LS-174T (ATCC No. CL 188) colon carcinoma cell line demonstrated the vast majority of cells express high levels of the D612-reactive antigen on their cell surface (FIG. 2). For contrast, FACS sorting of the LS-174T cell line is shown with monoclonal antibody CAA.

Flow cytometric analyses was done essentially as outlined in the methods of Greiner, J. W. et al, *Cancer Res.* 46:4984–4990 (1986) using an Ortho Cytofluorograf System 50H, with a blue laser excitation of 200 milliwatts at 488 nm. The cells were initially harvested, washed twice in $Ca^{+2}$ and $Mg^{+2}$ free Dulbecco's PBS. The cells ($10^6$/sample) were incubated for 30 minutes at 4° C. in the presence of 100 microliters of hybridoma tissue culture supernatant. Control cells were incubated in tissue culture supernatant harvested from NS-1 (ATCC No. TIB 18) cells. The cells were subsequently washed twice with $Ca^{+2}$ and $Mg^{+2}$ free PBS and incubated with 100 microliters of fluoresceniated goat anti-mouse IgG (1:32 dilution, Cappel Laboratories, Cochranville, Pa.) for 30 minutes at 4° C. The cells were washed, centrifuged at 500×g and resuspended at a concentration of $10^6$/0.3 ml PBS-glucose (1 gram glucose/liter $Ca^{+2}$ and $Mg^{+2}$ free PBS). The cells were fixed by adding 0.7 ml of either ice-cold 100% ethanol

TABLE 4

Binding of Monoclonal Antibody D612 to the Surface of Colon Carcinoma Cell Lines

| MAb | Dilution | Cell Surface Reactivity (cpm/5 × $10^4$ Cells) | | | | | | | |
|---|---|---|---|---|---|---|---|---|---|
| | | GEO | CBS | LS-174T | WiDr | DLD 1 | MIP | OVCAR-3[d] | A375[d] |
| D612[a] | undiluted | 6,914 | 8,916 | 4,834 | neg | neg | neg | neg | neg |
| | 1:5 | 6,758 | 8,247 | 4,457 | neg | neg | neg | neg | neg |
| | 1:25 | 5,741 | 6,817 | 3,865 | neg | neg | neg | neg | neg |
| | 1:125 | 5,242 | 4,222 | 2,639 | neg | neg | neg | neg | neg |
| | 1:625 | 1,454 | 1,929 | 1,689 | neg | neg | neg | neg | neg |
| | 1:3125 | neg | 888 | 1,022 | neg | neg | neg | neg | neg |
| | 1:15625 | neg | neg | 571 | neg | neg | neg | neg | neg |
| anti-HLA-DR[b] | | neg | NT[c] | 1,336 | NT | neg | neg | neg | 5,774 |

[a] Tissue culture supernatant;
[b] 20 nanograms/well;
[c] NT = not tested;
[d] OVCAR-3 (ATCC No. HTB 161) and A375 (ATCC No. CRL 1619) are human ovarian and melanoma cell lines, respectively.

The complete details of the radioimmunoassay, using live intact cells to measure the level of monoclonal antibody binding at the cell surface, have been published (see Colcher, D. et al, *Laboratory Research Methods in Biology and Medicine Immunodiagnostics*, New York, N.Y., Alan R. Liss, pp. 215–258 (1983)). Briefly, the human tumor cells were harvested from subconfluent T-75 flasks, transferred in the appropriate supplemented growth medium, and seeded in 96-well microtiter plates at a concentration of 1–5×$10^4$ cells/well. The cells were washed after which the appropriate concentration of primary purified monoclonal antibody was added for 1 hour. The $^{125}$I-labeled purified goat anti-mouse IgG was then added, after which the cells were washed and lysed with 2N NaOH and the radioactivity was counted in a gamma counter. The background radioactivity that consisted of cells that received no primary or an irrelevant antibody (i.e., MOPC-21, a mouse myeloma, Organon Technika, Cappel Labs, West Chester, Pa.) was approximately 200–400 counts per minute. Cells from 6–12 wells were routinely trypsinized and counted using a hemocytometer, and the reported activity represents a normalized value for 5×$10^4$ cells.

or 1% paraformaldehyde. Data from 25,000 cells were routinely analyzed.

EXAMPLE 6

Immunohistochemistry Studies

Initial studies on the use of monoclonal antibody D612 with formalin fixed tissue sections of human colon carcinomas demonstrated that the reactive determinant is destroyed by formalin fixation; all subsequent studies were thus conducted with frozen tissue sections. Indirect immunofluorescence was performed on acetone treated 4 micron cryostat sections of snap frozen tissues. The primary antibody (undiluted tissue culture supernatant) was incubated for 30 minutes at room temperature. The primary monoclonal antibody was removed by 3 washes in PBS. The slides were then incubated with fluoresceinated rabbit anti-mouse IgG (Cappel Labs, Cochranville, Pa.) for 30 minute followed by PBS washes.

Using an immunofluoresence assay and acetone fixed sections, it is shown in Table 5 that 85% of 27 primary colorectal carcinomas and 71% of 28 metastatic colorectal carcinomas are reactive at the plasma membrane with D612. Moreover, 12 of the 23 primary tumors and 11 of the 20 metastatic colorectal carcinomas displayed homogeneous staining in which virtually all the cells demonstrated staining along the plasma membrane with monoclonal antibody D612. Three of eleven stomach adenocarinoma also showed staining with D612. In contrast, all of over 90 non-gastrointestinal malignancies including over 70 carcinomas demostrated no or minimal staining (i.e., other than isolated cells) with monoclonal antibody D612. Only isolated areas of tumor cell reactivity were observed in the few tumors as indicated in Table 5 below.

TABLE 5

Reactivity of Monoclonal Antibody D612 with Frozen Sections of Neoplastic Tissues by Immunofluorescence Assay

| Tumor | Number +/Number Tested | Staining Patterns |
|---|---|---|
| Colorectal (primary) | 23/27 (85%) | Homogeneous (12), Heterogeneous (11) |
| Colorectal (metastatic) | 20/28 (71%) | Homogeneous (11), Heterogeneous (9) |
| Stomach | 3/11 | |
| Breast | 2/10 | Very Weak, Heterogeneous |
| Kidney | 0/6 | |
| Liver | 0/2 | |
| Brain | 2/9 | Isolated Cells |
| Skin | 0/5 | |
| Ovary | 3/17 | Mucinous Histotype, Heterogeneous |
| Lung | 2/10 | Isolated Areas |
| Parotid | 0/3 | |
| Prostate | 0/8 | |
| Urinary bladder | 0/5 | |
| Thyroid | 0/4 | |
| Soft tissues | 0/6 | |
| Melanocytes | 0/10 | |

The reactivity of monoclonal antibody D612 to colorectal carcinomas which have metastasized to different sites was also analyzed. As indicated in Table 6, the D612-reactive antigen was expressed in metastatic deposits at all the seven sites examined. Colorectal tumors with different degrees of differentiation were also examined for reactivity with monoclonal antibody D612.

TABLE 6

Reactivity of Monoclonal Antibody D612 to Frozen Sections of Colorectal Metastatic Foci using Immunofluorescence

| Patient | Site of metastases | Reactivity with MAb D612 |
|---|---|---|
| 1 | liver | 3/3[a] |
| 2 | liver | 2/2 |
| 3 | liver | 2/2 |
| 4 | liver | 0/4 |
| 5 | liver | 2/6 |
| 6 | subcutaneous | 3/3 |
| 7 | lymph node | 1/1 |
| 8 | ovary | 1/1 |
| 9 | ovary | 1/1 |
| 10 | lung | 1/2 |
| 11 | brain | 2/2 |
| 12 | pleural effusion | + |
| 13 | pleural effusion | + |
| 14 | pleural effusion | + |

[a]Number positive/number tested.

As seen in Table 7, well differentiated, moderately differentiated and poorly differentiated metastatic liver nodules of colorectal carcinoma all showed similar reactivity. This is in contrast with the results obtained with monoclonal antibody CAA and with anti-CEA monoclonal antibodies in which more reactivity is usually seen with well differentiated adenocarcinomas. A range of normal human tissues were also examined for reactivity with monoclonal antibody D612.

TABLE 7

Reactivity of Monoclonal Antibody D612 to Frozen Sections of Metastatic Liver Nodules in Colorectal Cancer Patients

| Degree of Differentiation of Tumor | No. of Patients | No. of Nodules Tested/Patient | D612 Reactivity |
|---|---|---|---|
| Well Diff. | 4 | 1 | positive homogeneous |
| Well Diff. | 1 | 1 | positive variable |
| Mod. Diff. | 3 | 1 | positive homogeneous |
| Mod. Diff. | 1 | 1 | positive variable |
| Mod. Diff. | 2 | 1 | negative |
| Mod. Diff. + Poorly Diff. | 1 | 3 | positive homogeneous |
| Mod. Diff. + Poorly Diff. | 2 | 2 | positive homogeneous |
| Mod. Diff. + Poorly Diff. | 1 | 6 | weakly positive |
| Poorly Diff. | 2 | 1 | positive homogeneous |

As seen in Table 8, all specimens of colon, rectum, duodenum, and ileum were positive as were three specimens of fetal colon. In contrast, the wide range of non-gastrointestinal tissues examined were all negative with monoclonal antibody D612 (Table 8).

TABLE 8

Reactivity of Monoclonal Antibody D612 using Immunofluorescence on Frozen Sections of Normal Human Tissues

| Tissues: | No. |
|---|---|
| Positive | |
| Colon | 8 |
| Rectum | 5 |
| Sigmoid | 2 |
| Duodenum | 1 |
| Ileum | 1 |
| Stomach: Gastric Glands | 1 |
| Fetal Colon (8, 10, 19 weeks) | 3 |
| Negative | |
| Lung (n = 4), Kidney (n = 3), Liver (n = 2), Lymph node (n = 1), Spleen (n = 1), Skin (n = 1), Brain Cortex (n = 1), Thymus (n = 1), Pancreas (n = 1), Urinary (n = 1), Bladder (n = 1), Endometrium (n = 1), Ovary (n = 1), Thyroid (n = 1), Prostate (n = 1). Smooth + Skeletal Muscle (n = 1), Testis (n = 1), Gall Bladder (n = 1), Esophagus (n = 1), Peripheral Blood Lymphocytes (n = 1), Myocardium (n = 1), Choroid Plexus (n = 1), Ureter (n = 1), Seminal Vesicle (n = 1), Fallopian Tube (n = 1) | |

For immunoperoxidase assays, 5 micron sections of frozen tissues were fixed in either cold methanol (4° C.) or cold acetone (4° C.) for 10 minutes, then incubated in methanol containing 0.3% $H_2O_2$ for 10 minutes to block endogenous peroxidase activity. After washing in PBS, the sections were treated with 10% normal horse serum. This and all subsequent reagents were diluted in PBS containing 0.1% BSA. The pretreatment serum was removed and sections were then incubated with purified immunoglobulin of primary monoclonal antibody D612 (4 micrograms/200 microliters). An isotype identical control monoclonal antibody UPC-10 (Organon Technika, Cappel Labs, West Chester, Pa.) was used as negative control, and was used concomitantly serial sections. After a 30 minute, room temperature incubation, the sections were washed in PBS and incubated with biotinylated horse anti-mouse IgG (Vector Laboratories, Inc., Burlingame, Calif.) for 30 minutes. The slides were again washed in PBS, then incubated with avidin DH and biotinylated horseradish peroxidase H complex (ABC) (Vector Laboratories, Inc.) for 30 minutes. After another PBS wash, the sections were treated with 0.06% diaminobenzidine (Sigma Chemical Co., St. Louis, Mo.) containing 0.01% $H_2O_2$ for 5 minutes. The sections were washed in distilled water and briefly counterstained with hematoxylin.

Each section was evaluated for the presence of epithelial brown diaminobenzidine precipitate indicative of MAb binding. Sections were scored + for clearly positive and + + for strongly positive. The sum of + and + + was used for total cellular reactivity. The approximate percentage of positive carcinoma cells was assigned according to the number of carcinoma cells positive divided by the total number of carcinoma cells present $\times 100$. For normal tissues the number of positive normal epithelial cells were divided by the total number of normal epithelial cells present $\times 100$.

Figure 3:
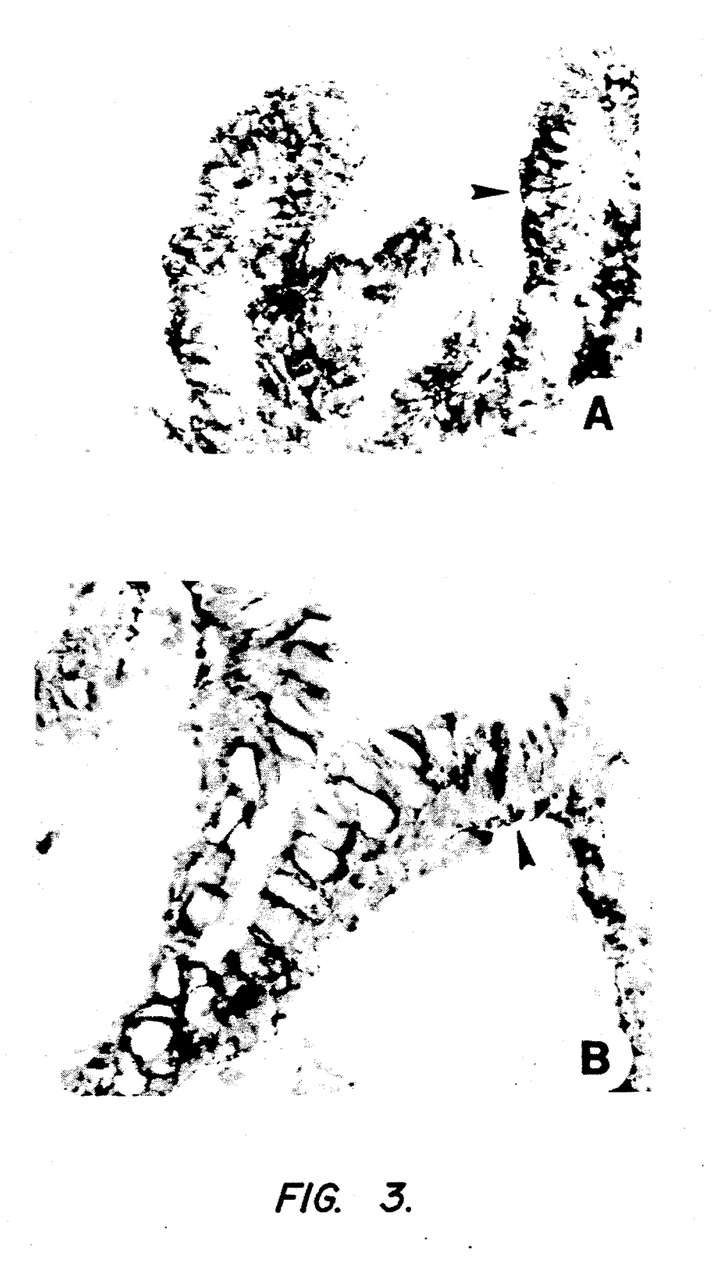
FIG. 3 is an immunoperoxidase stain of colon carcinoma (Panel A) and normal adult colon (Panel B) with monoclonal antibody D612. Note the intense homogeneous staining pattern located along the cytoplasmic membrane in the colon carcinoma (arrow, Panel A, magnification$\times 250$), and staining along the basolateral portion of the normal colon (arrow, Panel B, magnification$\times 500$).

Immunoperoxidase assays using the ABC technique were also utilized to examine the reactivity of monoclonal antibody D612 with frozen sections of normal adult tissues and colon carcinoma. The tissues used in these studies were different than those used in the immunofluorescence studies and the studies were conducted by different investigators. After an initial titration assay of a moderately differentiated colonic adenocarcinoma using methanol or acetone fixation, optimal staining conditions were chosen including cold methanol fixation and a primary monoclonal antibody incubation of 4 micrograms/200 microliters. As seen in Table 9, all 12 colon adenocarcinomas demonstrated D612 reactivity with many showing reactivity to the vast majority of tumor cells. The reactive antigen was present as finely granular deposits located along the entire cytoplasmic membrane (FIG. 3A). Reactive antigen was not detected in luminal secretions. One of 5 ovarian carcinomas showed minimal reactivity to approximately 10% of cells. Of 16 different types of normal tissues tested (Table 9) only colon and small bowel epithelium and gastric glands showed reactivity, whereas stomach surface epithelium was negative (Table 9). Colonic goblet cells and absorptive cells showed a homogeneous pattern of staining located primarily along the basolateral cytoplasmic membrane (FIG. 3B). Small bowel epithelium was reactive and showed the same cytoplasmic membrane distribution of staining. Reactivity of gastric epithelium was limited to parietal and chief cells and showed a diffuse cytoplasmic distribution.

TABLE 9

Reactivity of Monoclonal Antibody D612 with Frozen Sections of Colon Carcinoma and Adult Normal Tissues Using Immunoperoxidase Assays

| | | % Reactive Cells |
|---|---|---|
| Colon Carcinoma | | |
| A | moderately differentiated | >99 |
| B | moderately differentiated | >99 |
| C | moderately differentiated | 85 |
| D | moderately differentiated | 75 |
| E | moderately differentiated | 75 |
| F | moderately differentiated | 85 |
| G | moderately differentiated | 90 |
| H | moderately differentiated | 30 |
| I | moderately differentiated | 30 |
| J | moderately differentiated | 90 |
| K | poorly differentiated | 90 |

TABLE 9-continued

Reactivity of Monoclonal Antibody D612 with Frozen Sections of Colon Carcinoma and Adult Normal Tissues Using Immunoperoxidase Assays

| | | % Reactive Cells |
|---|---|---|
| L | poorly differentiated | 40 |
| Other Carcinomas | | |
| Pancreatic (n = 1) | | neg |
| Ovarian | | |
| Papillary Serous Cystadenocarcinoma (n = 3) | | neg |
| Mucinous (n = 1) | | neg |
| Mucinous (n = 1) | | 10 |
| Normal Adult Tissues: Positive | | |
| Colonic Epithelium, Small Bowel Epithelium, Stomach Gastric Glands (Parietal and Chief Cells Positive [n = 2], Gastric Surface Epithelium Negative [n = 5]) | | |
| Normal Adult Tissues: Negative | | |
| Kidney (n = 5), Spleen (n = 3), Bone Marrow (n = 1), PMN (n = 1), Thyroid (n = 1), Adrenal (n = 1), Pancreas (n = 1), Brain (n = 1), Heart (n = 1), Liver (n = 2), Esophagus (n = 1), Prostate (n = 1), Ovary (n = 1) | | |

EXAMPLE 7

In Vivo Carcinoma Targeting

Purified D612 IgG was labeled with $Na^{125}I$ by the Iodogen (Pierce, Rockford, Ill.) method, see Colcher, D. et al, Cancer Res. 44:5744-5751 (1984). Forty micrograms of the purified IgG was adjusted to 100 mM sodium phosphate (pH 7.2) and added to a $12 \times 75$ mm glass test tube that had been previously coated with 20 micrograms of Iodogen. Two minutes after the addition of 0.5 milliCuries of $Na^{125}I$ (DuPont-NEN, Boston, Mass.) the protein was removed from the tube and the unincorporated $^{125}I$ separated by gel filtration through a 10 ml column of Sephadex G-25 (Pharmacia, Piscataway, N.J.). The labeled antibody in the void of the column was pooled and diluted with PBS for in vivo studies. The iodination protocol resulted in $^{125}I$-labeled monoclonal antibody of approximately 5-10 microCuries/microgram with approximately 50% of the input iodine bound to protein.

Female athymic mice (nu/nu), obtained from the Frederick Cancer Research Facility at 4-6 weeks of age, were injected subcutaneously on the back with $1 \times 10^6$ LS-174T (ATCC No. CL 188) or A375 cells (ATCC No. CRL 1619) (0.2 ml). Animals were utilized for biodistribution studies approximately two weeks post-inoculation when the animals had tumors measuring between 0.5-0.8 cm in maximal diameter. Athymic mice bearing a human colon carcinoma xenograft (LS-174T) or human melanoma xenograft (A375) were injected i.v. with approximately 5 microCuries/mouse of $^{125}I$-D612 IgG. Mice were sacrificed by exsanguination at various times post-injection of the labeled monoclonal antibody. Blood, tumor and all the major organs were collected, wet weighed using an analytical balance and counted in a gamma counter. The percentage of the injected dose per gram (hereinafter "%ID/g") for each organ was determined and the radiolocalization indices (%ID/g in tumor divided by %ID/g in normal tissues) were calculated.

As seen in Table 10, a considerable fraction of the percent injected dose of the radiolabeled D612 per gram of tumor is detected at 24 and 72 hr, and at 7 days post antibody administration. In contrast, no localization of D612 IgG is detected on the A375 control tumor as compared to other organs (Table 10). The tumor to normal tissue ratios at 168 hours employing the LS-174T human colon carcinoma cell line (ATCC No. CRL 188) were 13:1 for liver, 12:1 for kidneys, 16:1 for normal colon, and between 7:1 and 9:1 for normal spleen, lung and heart. These studies demonstrate that radiolabeled D612 can bind to a human colon tumor in vivo within 24 hours, and can be detected for up to 7 days post monoclonal antibody administration.

TABLE 10

Biodistribution of $^{125}$I-D612 IgG in Athymic Mice Bearing Human Tumor Xenografts (% ID/g)

| Tissue | LS-174T | | | A375 | | |
|---|---|---|---|---|---|---|
| | 24 hrs | 72 hrs | 168 hrs | 24 hrs | 72 hrs | 168 hrs |
| Blood | 13.04 | 6.90 | 3.24 | 16.48 | 13.02 | 8.32 |
| Tumor | 19.25 | 26.67 | 15.29 | 5.70 | 5.56 | 4.68 |
| Liver | 3.58 | 2.74 | 1.23 | 3.96 | 3.32 | 2.64 |
| Spleen | 3.90 | 3.88 | 2.19 | 4.93 | 3.44 | 3.67 |
| Kidneys | 4.12 | 2.53 | 1.27 | 4.64 | 3.55 | 2.76 |
| Lungs | 5.71 | 3.96 | 2.04 | 11.67 | 7.02 | 5.61 |
| Heart | 4.43 | 3.24 | 1.64 | 5.54 | 5.44 | 5.05 |
| Colon | 2.64 | 2.05 | 0.98 | 2.97 | 2.43 | 2.59 |
| Pelvic Bone | 1.76 | 1.34 | 0.57 | 1.93 | 1.70 | 1.45 |

Athymic mice bearing a human colon carcinoma xenograft (LS-174T) or human melanoma xenograft (A375) were injected i.p. and sacrificed at the indicated times. The % ID/g for the various tissues were calculated.

Radiolabeled monoclonal antibodies can be used clinically to localize both primary and metastatic gastrointestinal lesions in situ. (It is known other anti-colon cancer monoclonal antibodies are also reactive with antigens expressed on normal colonic epithlium, such as anti-CEA monoclonal antibodies (see Mach, J. P. et al, N. Engl. J. Med. 303:5-10 (1980)) and monoclonal antibody 17-1A (see Chatal, J. F. et al, Hybridoma 5, Suppl. 1:S87-S96 (1986)). Both have been shown to be efficient in localizing colon carcinoma lesions). These findings may be due to the fact that: (a) the reactive antigens are not expressed on the surface of normal colonic epithelium and (b) the topography of normal colonic epithelium; a sheet of cells, does not make binding by a radiolabeled monoclonal antibody detectable by a gamma camera, as compared to the three dimensional structure of a carcinom mass. Radiolabeled monoclonal antibody D612 can also be used to detect metastatic carcinoma lesions in sites distal from colon such as the liver or lung. Since the reactive antigen is not shed, in situ diagnostic and therapeutic use of the antibodies is indicated.

EXAMPLE 8

Antibody Dependent Cell Mediated Cytotoxicity

Peripheral blood mononuclear cells were isolated from buffy coat preparations of normal donors by separation on Ficoll-Hypaque gradients (LSM, Organon Teknika, Durham, N.C.). Cells collected from the gradient interface were washed 4× with $Ca^{+2}$ and $Mg^{+2}$ free Dulbecco's PBS containing 2% fetal calf serum (GIBCO, Grand Island, N.Y.). Cells were cultured for 20 hours at $5 \times 10^6$/ml in RPMI 1640 medium supplemented with 2 mM L-glutamine, 100 Units/ml of penicillin, 100 micrograms/ml of streptomycin, and 10% heat-inactivated fetal calf serum (Grand Island Biological Co., Grand Island, N.Y.). Recombinant human IL-2 (Cetus Corporation, Emeryville, Calif.) (see Rosenberg, S. A. et al, Science 223:1412-1415 (1984)) was added to cultures at a final concentration of 100 Units/ml.

Target cells ($5-10 \times 10^6$) were labeled with 200 microCuries of sodium ($^{51}$Cr) chromate (250-500 milliCuries/milligram Cr; Amersham, Arlington Heights, Ill.) in 0.2 ml of fetal calf serum for 1 hour at 37° C. They were washed 3× in RPMI 1640, resuspended in complete medium, and then $1 \times 10^4$ cells in 50 microliters were added to 96-well U-bottom assay plates (Costar, Cambridge, Mass.), the wells of which contained 50 microliters of medium alone or various antibody preparations. Effector cells, which were harvested from flasks by scraping and washing once, were added immediately to the assay plates in a volume of 100 microliters. Effector to target ratios of 50, 25, 12.5, and 6.25 to 1 were assayed in the presence of 25, 5, 0.5 and 0.05 micrograms/ml of antibody. The plates were centrifuged for 3 minutes at 30×g, and then incubated for 4 hours at 37° C. in 7% $CO_2$. The plates were centrifuged as before prior to harvesting the supernatant for gamma counting using Skatron harvesting frames (Sterling, Va.). Experiments were carried out in triplicate; the standard deviation of replicates was less than 10%. Specific lysis was calculated using the formula:

$$\% \text{ lysis} = \frac{\text{observed cpm} - \text{background cpm}}{\text{total cpm} - \text{background cpm}} \times 100$$

Background cpm were obtained from radioactivity released by target cells incubated in medium alone, which was between 5 to 10% of the total released after treatment of target cells with 2.5% Triton X-100.

Table 11 shows that monoclonal antibody D612 was capable of mediating antibody dependent cell-mediated cytotoxicity against the LS-174T colon tumor cell line (ATCC No. CRL 188) while no specific lysis was obtained with the antigen-negative ovarian carcinoma cell line, OVCAR-3 (ATCC No. HTB 161) Antibody dependent cell-mediated cytotoxic activity was observed with effectors that were either unexposed to or were treated with exogenous IL-2. As expected, IL-2 activation caused an increase in cytolytic activity against both tumor targets in the absence of antibody. The increase in killing of LS-174T cells induced by IL-2 in the absence of antibody approximated cell lysis obtained with untreated effectors in combination with antibody. Upon the addition of D612 antibody to IL-2 activated effectors, cytotoxicity was augmented, approaching 70 to 80% lysis at the higher effector to target cell ratios examined. Enhancement of antibody dependent cell-mediated cytotoxicity by IL-2 activation was most obvious at the lower effector:target cell ratios. Similar levels of antibody dependent cell-mediated cytotoxic activity were maintained with either untreated or IL-2 activated effectors when the D612 antibody was used at a concentration down to 0.5 micrograms/ml.

TABLE 11

Antibody Dependent Cell-Mediated Cytotoxic Activity of D612 Against Colon and Ovarian Carcinoma Cell Lines Using Human Effector Cells

| MAb | IL-2 Activation | Effector to Target Ratio | | | | | | | |
|---|---|---|---|---|---|---|---|---|---|
| | | 50:1 | | 25:1 | | 12.5:1 | | 6.25:1 | |
| | | LS-174T | OVCAR-3 | LS-174T | OVCAR-3 | LS-174T | OVCAR-3 | LS-174T | OVCAR-3 |
| None | — | 6 | 6 | 1 | 1 | 1 | 1 | 1 | 1 |
| MOPC-21 | — | 5 | 4 | 1 | 1 | 1 | 1 | 1 | 1 |

TABLE 11-continued

Antibody Dependent Cell-Mediated Cytotoxic Activity of D612 Against Colon and Ovarian Carcinoma Cell Lines Using Human Effector Cells

| MAb | IL-2 Activation | Effector to Target Ratio | | | | | | | |
|---|---|---|---|---|---|---|---|---|---|
| | | 50:1 | | 25:1 | | 12.5:1 | | 6.25:1 | |
| | | LS-174T | OVCAR-3 | LS-174T | OVCAR-3 | LS-174T | OVCAR-3 | LS-174T | OVCAR-3 |
| COL-1 | — | 6 | 8 | 2 | 2 | 1 | 1 | 1 | 1 |
| D612 | — | 42 | 5 | 30 | 1 | 16 | 1 | 8 | 1 |
| None | + | 38 | 53 | 22 | 33 | 11 | 21 | 5 | 10 |
| MOPC-21 | + | 33 | 52 | 23 | 34 | 10 | 16 | 6 | 10 |
| COL-1 | + | 42 | 62 | 27 | 37 | 11 | 20 | 7 | 12 |
| D612 | + | 77 | 53 | 66 | 35 | 44 | 18 | 26 | 10 |

Peripheral blood mononuclear cells from a healthy donor were used as effector cells after incubation for 20 hours in the absence or presence of 100 Units/ml of IL-2. (see Rosenberg, S.A. et al, Science 223:1412–1415 (1984)). Results are depicted as percent specific lysis obtained in a 4 hour chromium-release assay using a concentration of monoclonal antibody of 5 micrograms/ml.

A pharmaceutical composition comprising the monoclonal antibodies of the present invention in a pharmaceutically acceptable, non-toxic, sterile carrier such as physiological saline, non-toxic buffers and the like, now also becomes possible. The amount of said antibodies in the pharmaceutical composition should be sufficient to achieve effective binding with the antigen against which said antibodies have specific affinity or neutralization reactivity. The pharmaceutical composition may be administered in a single or multiple dosage with other adjuvants or additives, if necessary, in any suitable manner to the host in need of said antibodies.

The composition of the invention can be packaged in kits for use in diagnosis and evaluation of the disease process. Compositions of matter comprising antibodies attached to solid supports are particularly convenient for use in test kits. Antibodies attached to imaging or detection markers are particularly useful for such purposes.

While this invention has been described in detail and with reference to specific embodiments thereof, it will be apparent to one skilled in the art that various changes and modifications could be made therein without departing from the spirit and scope thereof.

What is claimed is:

1. A hybridoma assigned A.T.C.C. Accession No. HB 9796 which produces the monoclonal antibody designated D612 which immunologically binds to human gatrointestinal cancers and normal gastrointestinal epithelium, and not other cancers or other normal human tissues.

2. Monoclonal antibodies having all the identifying characteristics of the antibodies produced by the hybridoma cell line assigned A.T.C.C. Accession No. HB 9796, immunoreactive fragments, recombinants or chimerics thereof, which immunologically bind to human gastrointestinal cancers and normal gastrointestinal epithelium, and not other cancers or normal human tissues.

3. Monoclonal antibodies according to claim 2 having all the identifying characteristics of the antibodies produced by the hybridoma cell line assigned the A.T.C.C. Accession No. HB 9796, immunoreactive fragments or chimerics thereof, which immunologically bind to human gastrointestinal cancers and normal gastrointestinal epithelium, and not other cancers or normal human tissues.

4. Monoclonal antibodies according to claim 2 having all the identifying characteristics of the antibodies produced by the hybridoma cell line assigned the A.T.C.C. Accession No. HB 9796, immunoreactive fragments or recombinants thereof, which immunologically bind to human gastrointestinal cancers and normal gastrointestinal epithelium, and not other cancers or normal human tissues.

5. The monoclonal antibody of claim 2, which immunologically binds to a 48,000 molecular weight glycoprotein found on the surface of colon cancer cells.

6. Monoclonal antibodies of claim 2, obtained from a hybridoma selected from the group consisting of hybridomas having all the identifying characteristics of A.T.C.C. No. HB 9796.

7. Monoclonal antibodies of claim 2, wherein said antibodies are of an $IgG_{2a}$ isotype.

8. Monoclonal antibodies of claim 2, wherein said antibodies are conjugated to a label, a tumor detecting marker or to a therapeutic agent.

9. Monoclonal antibodies of claim 8, wherein said label is selected from the group consisting of a radioisotope, a fluorescent molecule and an enzyme.

10. Monoclonal antibodies of claim 9, wherein said radioisotope is selected from the group consisting of $^{32}P$, $^{14}C$, $^{3}H$, $^{125}I$ and $^{35}S$.

11. Monoclonal antibodies of claim 9, wherein said fluorescent molecule is selected from the group consisting of fluorescein and rhodamine.

12. Monoclonal antibodies of claim 9, wherein said enzyme is selected from the group consisting of alkaline phosphatase and horseradish peroxidase.

13. Monoclonal antibodies of claim 8, wherein said tumor detecting marker is selected from the group consisting of $^{125}I$, $^{131}I$, $^{123}I$, $^{111}In$, $^{67}Ga$, $^{68}Ga$, $^{99m}Tc$ and Gd.

14. Monoclonal antibodies of claim 8, wherein said therapeutic agent is selected from the group consisting of a radionuclide, drug, toxin and second antibody.

15. Monoclonal antibodies of claim 14, wherein said radionuclide is selected from the group consisting of $^{131}I$, $^{90}Y$, $^{105}Rh$, $^{47}Sc$, $^{67}Cu$, $^{212}Bi$ and $^{211}At$.

16. Monoclonal antibodies of claim 14, wherein said drug is selected from the group consisting of methotrexate and adriamycin.

17. A composition of matter comprising antibodies of claim 2, in a carrier.

18. A composition of matter comprising antibodies of claim 2, attached to a solid support.

19. A method of producing anti-idiotype antibodies by administration of an immunogenic effective amount of the composition of claim 17, to a mammal and recovering said anti-idiotype antibodies.

* * * * *